(12) United States Patent
Hartle et al.

(10) Patent No.: US 7,144,737 B2
(45) Date of Patent: Dec. 5, 2006

(54) PROCESS FOR DETERMINING THE PERCENT OF CHELATION IN A DRY MIXTURE

(75) Inventors: Jennifer Hartle, Harrisville, UT (US); Clayton Ericson, Morgan, UT (US); Stephen D. Ashmead, Clinton, UT (US)

(73) Assignee: Albion International, Inc.

( * ) Notice: Subject to any disclaimer, the term of this patent is extended or adjusted under 35 U.S.C. 154(b) by 451 days.

(21) Appl. No.: 10/245,826

(22) Filed: Sep. 17, 2002

(65) Prior Publication Data

US 2003/0138963 A1 Jul. 24, 2003

Related U.S. Application Data

(60) Provisional application No. 60/322,894, filed on Sep. 17, 2001.

(51) Int. Cl.
*G01N 33/00* (2006.01)

(52) U.S. Cl. .......................................... 436/86; 436/89

(58) Field of Classification Search ................... 436/86, 436/89

See application file for complete search history.

*Primary Examiner*—Monique T. Cole
(74) *Attorney, Agent, or Firm*—Thorpe North & Western

(57) ABSTRACT

A method for determining the amount of metal amino acid chelate present in various chelate compositions. FT-IR is used to determine the amount of free amino acid present. The bound amino acids may be in the form of an amino acid complex or an amino acid chelate. A total metal analysis and measurement of ligand quantity is then performed, from which the percent of metal amino acid chelate in the sample is calculated.

9 Claims, No Drawings

PROCESS FOR DETERMINING THE PERCENT OF CHELATION IN A DRY MIXTURE

REFERENCE TO RELATED APPLICATION

This application claims the benefit of U.S. Provisional Application No. 60/322,894 filed Sep. 17, 2001.

BACKGROUND OF THE INVENTION

The present invention relates generally to methods for assaying chelate compositions. More particularly, the present invention relates to determining the amount of metal amino acid chelate in a given sample.

SUMMARY OF THE INVENTION

It has been recognized that it would be advantageous to develop a reliable and accurate process for determining the percent of chelation in a metal amino acid chelate composition.

In accordance with one aspect of the present invention a composition containing a known amount of amino acid and mineral is provided. A method such as FT-IR is used to determine the amount of free amino acid in the composition from which the percent of bound amino acid is calculated. Using further testing in the form of a total metal analysis, such as ICP-MS, the total mineral content is determined. The total nitrogen content is also determined and using information provided by the manufacturer of the amino acid the total available ligand for binding content is determined. The amount of bound ligand content relative to the total mineral is then easily determined using the previously calculated percent of bound amino acid. Based on the assumption that available ligands will bind to mineral first in a one-to-one ratio and the remaining ligands will bind in a two-to-one ratio the percent chelation may be determined. Specifically, by deduction, and the use of chemical principles, one can deduce that the only element present in the mixture that the ligand could be bound to is the mineral in question.

In accordance with a more detailed aspect of the present invention the amino acid is glycine and the mineral is copper.

Additional features and advantages of the invention will be apparent from the detailed description which follows, taken in conjunction with the accompanying drawings, which together illustrate, by way of example, features of the invention.

DETAILED DESCRIPTION

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention is drawn to determining the amount of metal amino acid chelate present in various amino acid chelate compositions, including powdered amino acid chelates. In a preferred embodiment, using glycine as the amino acid, the method specifically shows the amount of free glycine in the mixture. By subtraction from the total amount of glycine in the sample, the amount of bound glycine is determined. By deduction, and the use of chemical principles, one can deduce that the only element present in the mixture that the ligand could be bound to is the mineral in question. Therefore, knowing the amount of mineral initially present and by simple subtraction, the method not only shows the amount of an amino acid ligand bound in a chelate, but also the amount of free mineral in a mixture.

This process uses FT-IR technology to determine the difference between the chelate bonds and the presence of free glycine, or other amino acid ligand(s) in a metal amino acid chelate. Other naturally occurring amino acids include glycine, alanine, arginine, asparagine, aspartic acid, cysteine, cystine, glutamine, glutamic acid, histidine, hydroxyproline, isoleucine, leucine, lysine, methionine, ornithine, phenylalanine, proline, serine, threonine, tryptophan, tyrosine, valine, and combinations thereof. There are differences in the bonding characteristics of a chelate and a free amino acid that are detectable by FT-IR. For example, free glycine exhibits a peak at 504 cm$^{-1}$ that disappears as the amino acid becomes bound to the mineral. Glycine has an apparent peak at 504 wavenumbers as noted in *Infrared and Raman Spectra of Inorganic and Coordination Compounds,* Fourth Edition, Nakamoto, Kazuo, John Wiley & Sons, Inc., New York, 1986. This indicates a rocking motion due to the terminal COO$^{31}$. As one or more glycine(s) become bound by a metal, the rocking of the carbonyl group is immobilized, and thus the band disappears in a linear fashion as the amount of unbound glycine in the sample decreases. By measuring the absorbance of this peak and comparing it to the absorbance of glycine standards at the same wavenumber, the amount of free ligand in the sample can be ascertained. Then, by subtraction from the total amount of ligand in the mixture, the amount of bound ligand can be determined.

Since non-complexed metal cations cannot be detected using FT-IR, further analysis is desired to show that there is not excess metal present in the sample containing chelates. When the FT-IR method described above is coupled to a total metal analysis, performed on, for example, an ICP-MS, and a measurement of ligand quantity (such as percent of nitrogen) is provided, then a larger picture can be seen. Although copper is described herein, other minerals would also be suitable to the present invention and include without limitation copper, zinc, manganese, iron, magnesium, cobalt, chromium, molybdenum, and combinations thereof.

As one part of the method utilizes the measurement of amount of free amino acid in the chelate, the presence of amino acid in the sample can be proven before the other steps in the process are carried forth. With respect to a preferred embodiment, if it is known that glycine is used as the ligand, an amino acid analysis of the samples need not be performed. However, if this method were to be used on products of unknown ligand content, an amino acid analysis should be performed prior to the FT-IR procedure outlined herein. The amino acid analysis used should be one where the amount of amino acid in the sample can be quantified. If a sample containing no, or very little amino acid is analyzed by the following procedure, it could appear to be completely chelated when that may not be the case. For simplicity, the present process is exemplified using glycine. However, it could also be used for other amino acid chelates, provided appropriate research and testing was conducted to validate the peak assignment for that particular amino acid due to chelation.

A metal chelate may be defined as "a substance [combined] with [a] metal containing two or more donor groups so that one or more rings are formed." *Chemistry of the Metal Chelate Compounds,* Martell, Arthur E., Calvin, Melvin, Prentice-Hall, Inc., New York, 1952. By this definition, a chelate can contain one or more ligands. Dr. Robert D. Hancock, Ph.D., D.Sc., defines a chelating ligand as, "A ligand that contains more than one donor atom which donor atoms are coordinated to a single metal ion to form one or more ring structures containing a metal ion." *Metal Complexes in Aqueous Solutions,* Martell, Arthur E., Hancock, Robert D., Plenum Press, New York, 1996. Therefore, a metal combined with a ligand in a 1:1 ratio can be considered a chelate as long as a ring structure is formed. Martell also notes that the bonds in a chelate are "essentially covalent," indicating the metal chelates have properties much different than those of the metal sulfates, which are bonded ionically.

Conversely, a unidentate metal complex is defined as a ligand combined with a metal in which there are no ring structures formed. One would be led to wonder then, how to tell the difference between a metal amino acid chelate and a metal amino acid complex. Nakamoto, supra, indicates that the difference is detectable when one looks at the IR scans of the different species. He states, "The bidentate (chelated) glycino group absorbs at 1643 $cm^{-1}$, unlike either the ionized unidentate group (1610 $cm^{-1}$) or the unionized unidentate group (1710 $cm^{-1}$)." According to the present invention, glycine metal amino acid chelates demonstrate strong peaks at 1643 $cm^{-1}$, indicating bidentate chelates. The actual value of the peak at 1643 $cm^{-1}$ may vary somewhat due to the nature of the particular metal to which the glycine is bound.

As the analysis of percent of chelation is discussed, it can be noted that when testing powdered materials, the analysis should be carried out in a solid state. This is because the configuration of the molecules in a powdered chelate state can change dramatically when introduced to an aqueous environment. As noted by Dr. Robert Hancock, Ph.D., D.Sc., any analyses of a metal amino acid combination carried out in solution will therefore not necessarily relate to a composition having the same metal and amino acid ratios in the solid state. This is largely because a dry mixture of a metal salt mixed with an accompanying ligand in the appropriate molar ratios could appear to be chelated when introduced to an aqueous environment, when in fact, they may not be bound in the solid state as would be the case with a chelate.

Another factor influencing aqueous state evaluation is that the solutions can easily be manipulated to give favorable results by controlling pH. As shown in the book entitled *Metal Complexes in Aqueous Solutions,* by Martell and Hancock (1996), the pH of the solution, molar ratios, and concentration of the complex, dramatically affect the state in which the metal complex can be found. Since powdered chelates are not in an aqueous environment when they are sold, an aqueous analysis of the products would be inaccurate and could be largely misconstrued.

A number of biological experiments have been carried out to determine the absorption of amino acid chelates compared to nonchelated mineral salts. It has been determined by several studies that amino acid chelates have been shown to be absorbed and incorporated more readily than the nonchelated mineral salt of the same mineral. In fact, in the book *Intestinal Absorption of Metal Ions and Chelates,* Ashmead, H. DeWayne, Graff, Darrell J., Ashmead, Harvey H., Charles C. Thomas Publisher, Illinois (1985), states, "The metals are not absorbed or metabolized as isolated ions, but instead bonded to organic molecules." This statement indicates that for metals to be absorbed at all, they are likely bound organically. This binding can take place in the stomach prior to digestion. However, many studies, as noted by Ashmead, supra, show that metal amino acid chelates are utilized in biological systems more readily than metals in an ionic state. The increased utilization and physiological response of these chelated mineral supplements can be largely attributed to the fact that the minerals are chelated to organic ligands, namely amino acids, prior to ingestion.

Other references of interest include: *Chelated Mineral Nutrition in Plants, Animals and Man,* Ashmead, H. DeWayne, Charles C Thomas Publisher, Illinois, 1982; *Test Methods for Evaluating Solid Waste Physical/Chemical Methods,* USEPA, SW-846, June 1997 Final Update III, Method 3050B; *Test Methods for Evaluating Solid Waste Physical/Chemical Methods,* USEPA, SW-846, June 1997 Final Update III, Method 6020; and *Calcium Containing Finished Product Lead Testing Protocol for Inductively Coupled Plasma Mass Spectrometry (ICP-MS) Procedure,* California State Laboratory Standard Operation Procedure, California Proposition 65.

EXAMPLE

The methods of the present invention are carried out by following the method steps and/or equivalent steps described herein. However, it should be noted that these steps produce accurate results provided the operators have full knowledge of how to operate the instruments used. The methods described herein provide examples for carrying out the present invention, and are not intended to be limiting. In other words, certain specific amounts, temperatures, mixing procedures, equipment, etc., are used for convenience only. One skilled in the art would recognize that modifications of these and other parameters would yield similar accurate results. Further, though the steps below are described precisely as to what "should" be done or what "is" done, this language is not to be construed that any specific step per se is critical to the respective method.

Step 1: FT-IR Method

The following method is a potassium bromide (KBr) pellet method; however, other equivalent methods can be used.

Materials and equipment used:
  Drying Oven set at 105° C. (FISHER ISOTEMP)
  FT-IR grade KBr (available from Acros Chemical)
  Glycine (available as SIGMA ULTRA PURE)
  100 milliliter beakers
  Borosilicate Scintillation vials with tight closures
  Dessicator
  Dessicated storage chamber
  Analytical balance accurate to 0.0001 grams
  13 millimeter KBr Die Set
  Carver Model C Press
  Amalgamator (DENTSPLY PROMIX)
  Crescent Capsule and Pestle—The capsule needs to be the right size for the
  Promix amalgamator
  Spectrophotometer (MATTSON 3020 FT-IR with WIN-FIRST FT-IR Software v.3.5)

Step 1.1—Drying

This drying procedure is to be followed for all samples to be run on the IR including technical samples, standards, internal standards and FT-IR grade KBr.

Place ten grams of sample in a clean, dry 100-milliliter beaker. Place the beaker in a drying oven set at 105° C. After the sample has dried for a minimum of four hours, preferably overnight, remove from the drying oven using forceps and immediately place in a dessicator to cool at room temperature. In this embodiment, the samples are placed in the dessicator immediately after removal from the oven so the samples don't absorb moisture from the atmosphere. Excess moisture in the sample can cause unwanted noise in the IR spectrum. It should be noted that longer drying times may be needed depending on environmental conditions and moisture content of the sample being dried. One should preferably verify the dryness of the sample prior to using.

After cooling, transfer the sample from the beaker to a clean, dry scintillation vial and 2-5 store in a dessicated storage chamber. No clean up of the samples is necessary as the FT-IR method looks only at a specific bond present in the ligand used in chelation. Since any excess ligand could be washed away in a clean-up step, and because the methods contemplate the measurement of the amount of excess ligand in the sample, a clean up step is not a preferred course of action.

Step 1.2—Standard Curve and Sample Preparation

A six point standard curve ranging from 0.0078% to 0.5000% glycine is prepared using Glycine (ULTRA PURE available from Sigma Chemicals) and infrared grade KBr (Acros Chemical). Using an analytical balance accurate to 0.0001 grams, the samples are weighed to provide 0.0078%, 0.0156%, 0.0313%, 0.0625%, 0.1250%, 0.2500%, and 0.5000% glycine in KBr. For purposes of the present example, the samples are prepared using a stock mixture, which are completely homogenized. Subsequent samples are weighed from the stock mixture using successive dilutions.

Sample Preparation

Using an analytical balance accurate to 0.0001 grams, the sample to be analyzed is weighed to 1.00% in KBr. There should be at least 150 mg of the sample prepared for pellet preparation. In most cases, one gram of each sample should be prepared.

Pellet Preparation

For both the standards and samples to be tested, the pellet making process can be the same. After the samples are accurately weighed to 1.00% in KBr, they are transferred to a Crescent capsule containing a pestle (stainless steel ball). The cap onto the capsule is then twisted and checked for a proper seal. The capsule is then placed in the amalgamator. Using the fastest agitation setting, the sample is shaken for thirty seconds. The sample should be completely homogenous. Next, 150 milligrams of the homogenate is weighed using an analytical balance accurate to 0.001 grams. Any excess homogenate can be transferred to a scintillation vial and placed in a dessicated storage chamber for later use.

The 150 mg of homogenate is transferred to a 13 mm vacuable KBr die and smoothed flat in the die using the die plunger, making sure not to lose any of the powder. The die is assembled and pressed in a Carver Model C press twice at six metric tons of pressure for thirty seconds each time. The resulting pellet should be circular and translucent. If the pellet is not clear (opaque) in sections or not a complete circle, it should be remade until an appropriate sample is obtained.

Step 1.3—FT-IR analysis

This procedure assumes that the FT-IR has been properly tuned and validated and that a background has been run. The pellet previously prepared is transferred to the pellet holder without the face of the pellet being touched. The pellet holder is placed in the sample chamber of the FT-IR, where the sample is scanned thirty-two times from 4000-400 $cm^{-1}$ at a resolution of 4 $cm^{-1}$. The moving mirror in the FT-IR should be set at a scanning velocity of 10 megahertz. The resulting scan can be saved for later analysis, described below.

Step 2: ICP-MS Method

The following method is an inductively coupled plasma-mass spectrometer (ICP-MS) method; however, titration methods or atomic absorption methods for metal assay are also available, as well as other equivalent methods.

Materials and Equipment Used

Digestion Vessels—70-milliliter polypropylene digestion vessels with graduated marks for volume Laboratory grinder Vapor recovery device (e.g. ribbed watch glasses, appropriate refluxing device)

Temperature measurement device capable of measuring to at least 125° C. with suitable precision and accuracy Centrifuge and centrifuge tubes (50 milliliter) Centrifuge tubes should be tested to show that volumetric markings are accurate to less than 0.5% error. FISHER brand 0.50 milliliter freestanding tubes (Cat. #14-375-150) are able to meet this requirement Analytical balance—capable of accurate weightings to 0.001 grams Heating Source—Block Digester capable of maintaining a constant temperature of 95 ±5° C.

Reagent Water—Deionized water with 18-megaohm resistivity

Concentrated Nitric Acid ($HNO_3$)—Certified ACS Plus grade

Concentrated Hydrochloric Acid (HCl)—Certified ACS Plus grade

Standard Stock solutions may be purchased or prepared from ultra high purity grade chemicals or metals (99.99% or greater purity)—Used for instrument calibration and verification Internal standard solution—2 ppm of $Li^6$ 95% enriched isotope, Bi, Ho, In, Sc, Tb, Y, and Ge Tuning solution—10 ppb of Ce, Ti, Y, and Li The quality control standard is the initial calibration verification solution (ICV), which is preferably prepared in the same acid concentrations as the calibration standards—This solution can be an independent standard (second source) and near the midpoint of the linear calibration range Inductively coupled plasma-mass spectrometer A system capable of providing resolution, better than or equal to 1 amu at 10% peak height is required. The system should have a mass range from at least 6 to 240 amu and a data system that allows corrections for isobaric interferences and the application of the internal standard technique Argon gas supply: high purity grade (99.9%)

Step 2.1—Sample Digestion

Mix the sample to be tested thoroughly to achieve homogeneity. Some samples may require additional grinding to attain homogeneity. This can be accomplished by placing a small amount of sample in a clean dry laboratory grinder and grind until sample has attained the desired level of homogeneity. Continue processing sample until entire sample is ground. Mix sample thoroughly.

A 0.5 gram sample is weighed to the nearest 0.001 grams into a 70-milliliter digestion vessel. Five milliliters of concentrated $HNO_3$ is added to the sample, the slurry is mixed and covered with a watch glass or vapor-recovering device. The sample is heated to 95±5° C. for 15 to 20 minutes. Vapor should be colorless before the sample is removed from the heating source and allowed to cool to room temperature.

Dilute the sample to fifty milliliters using the graduations on the digestion vessel. For samples with excessive undigested material, filtration through a Whatman No. 41 filter paper (or equivalent) may be desired.

Step 2.2—ICP-MS analysis

Operation conditions for the ICP-MS: The analyst should follow the instructions provided by the instrument manufacturer. The instrument should be allowed to thermally stabilize about thirty minutes prior to instrument tuning and sample analysis.

Instrument tuning

Mass calibrations in the mass regions of interest are required prior to sample analysis. If the mass calibration differs more than 0.1 amu from the true value, then the mass calibration can be adjusted to the correct value. The resolution can also be verified to be less than 0.9-amu full width at 10 percent peak height.

Oxides are the ratio of mass $^{156}CeO$ divided by mass $^{140}Ce$. If oxides are above 3%, adjustments can be made to minimize oxide levels to less than 3%.

Doubly charged ions are the ratio of mass $^{70}Ce^{++}$ divided by mass $^{140}Ce$. The double charged value is preferably less than 3%. Values above 3% require adjustments to reduce the doubly charged ions to less than 3%.

All of the above tuning requirements are preferably met before instrument calibration and sample analysis.

The instrument for the analytes of interest can be calibrated using a calibration blank and several calibration standards. Immediately after calibration, it is preferable that the calibration be verified using the ICV standard. When measurements exceed ±10% of the accepted value, the analysis can be terminated, the problem corrected, and then the instrument recalibrated. Three integrations of the solutions should be analyzed.

Samples should be analyzed using the same conditions as calibration standards. For best results, the calibration should be checked every 10 samples and after the last sample. Any measurement exceeding +10% constitutes a non-conformance and analytical results for that isotope should be discarded.

Step 3: Data Analysis

Step 3.1—FT-IR

To analyze the scans obtained by the FT-IR, several steps are taken. In the present embodiment, all steps are taken within the software provided with the spectrophotometer. If the sample was previously saved, it should be loaded into the software package. First, the scan can be smoothed with a Boxcar 3 method to remove noise from the spectrum. Next, the scan can be autobaselined and converted from transmittance into absorbance, if necessary. Once this has been done, the 504 $cm^{-1}$ peak can be assessed. To find the absorbance of the peak, the off-peak annotator can be used. The resulting scan including the peak report can be printed for analysis. The absorbance data can then be entered into a spreadsheet for further evaluation.

Calculations

Standard Curve

First, a standard curve is prepared using the glycine standards run on the FT-IR described previously. The following is given by way of example, wherein the absorbances of the glycine standards are shown in Table 1.

TABLE 1

| Sample # | Glycine (g) | KBr (g) | Total (g) | % Glycine | Absorbance (504 $cm^{-1}$) |
|---|---|---|---|---|---|
| 1 | 0.0100 | 0.9900 | 1.0000 | 1.0000% | n/a |
| | | Previous Sample (g) | | | |
| 2 | 0.5002 | 0.5005 | 1.0007 | 0.4999% | 0.60 |
| 3 | 0.5003 | 0.4998 | 1.0001 | 0.2501% | 0.34 |
| 4 | 0.5001 | 0.5000 | 1.0001 | 0.1250% | 0.16 |
| 5 | 0.5004 | 0.5002 | 1.0006 | 0.0625% | 0.08 |
| 6 | 0.5000 | 0.5000 | 1.0000 | 0.0313% | 0.03 |
| 7 | 0.5003 | 0.4998 | 1.0001 | 0.0156% | 0.02 |
| 8 | 0.5002 | 0.5003 | 1.0005 | 0.0078% | 0.02 |

Note: The above samples were made using subsequent dilutions of each sample. For example, sample 2 was made using 0.5 g of sample 1 and 0.5 g KBr, sample 3 was made using 0.5 g of sample 2 and 0.5 g KBr, etc. The samples were substantially homogenized before making subsequent samples.

The absorbances are then plotted against the percent concentration and the equation of the line was obtained using standard linear regression. The resulting equation of the standard curve is y=121.6x+0.0062, where y is the absorbance at 504 $cm^{-1}$ and x is the concentration of free ligand in the sample. The corresponding correlation coefficient is 0.9953, which is adequate for quantification, the equation of the line is then used to determine the amount of free ligand in the metal amino acid chelates.

Sample Free-Ligand Determination

As an example, a sample of Albion Laboratories Copper Mineral Amino Acid Chelate Lot #90821 (Cu 90821) exhibited an absorbance of y=0.02. To determine the amount of free glycine in this sample, the absorbance value is inserted into the equation, $$y=121.6x+0.0062$$

$$x=(y-0.0062)/121.6$$

$$x=(0.02-0.0062)/121.6$$

$$x=0.0113$$

Of the 1.00% sample, 0.0113% of the glycine is free; indicating that 1.13% of the glycine in the total sample is unbound. Therefore, by simple subtraction, 98.87% of the glycine in the chelate is bound to the metal.

Determination of Unbound Metal in Sample

The metal content of the aforementioned copper sample was determined by the ICP-MS to be 10.09% Cu. Because there were other non-ligand nitrogen containing additives in the metal amino acid chelates, a total nitrogen assay would not be adequate to give an indication of the amount of glycine present in the assay. Therefore, the manufacturer should provide the percent of nitrogen due to the ligand as calculated from the formulation of the product. This number will be considered to be constant, although each different element will have it's own constant number, as each have their unique formulations. For example, the percent of nitrogen due to ligand in Cu 90821 provided by Albion Laboratories, Inc. is 2.6957%. Once the percent metal and percent nitrogen due to ligand are known, the amount of unbound metal in the sample can be calculated.

First, a metal to ligand ratio is determined. To find this ratio, the number of moles of both copper and ligand are determined in 100 grams of sample and compared.

$$\frac{10.09 \text{ g Cu}}{100 \text{ g Chelate}} \times \frac{1 \text{ mole Cu}}{63.546 \text{ g Cu}} = \frac{0.1588 \text{ mol Cu}}{100 \text{ g Chelate}}$$

$$\frac{2.6957 \text{ g N}}{100 \text{ g Chelate}} \times \frac{1 \text{ mole N}}{14.0067 \text{ g N}} \times \frac{1 \text{ mole glycine}}{1 \text{ mole N}} = \frac{0.1925 \text{ mol glycine}}{100 \text{ g Chelate}}$$

Therefore, the metal to ligand ratio is: 0.1588:0.1925 or 1:1.2122 Since the amount of bound glycine is known, using the metal to ligand ratio, the amount of unbound metal can be determined. It is believed that the metal forms a 1:1 chelate with the ligand first, then after all of the metal is bound in a 1:1 ratio, the 1:2 chelate is formed. With this in mind, the calculations for the example of the Cu 90821 are follows:

Because a 1:1 chelate forms initially, it is assumed that all of the bound glycine is bound to the copper in a 1:1 ratio. The amount of glycine available for binding is 98.87% of the total. Therefore, the following calculation can be made.

1.2122×0.9887=1.1985

The metal to binding ligand ratio is then considered to be 1:1.1985. Therefore, the metal would be 100% bound by the glycine in a 1:1 metal to ligand ratio, with excess bound glycine also bound to the metal in a 1:2 ratio. Thus, in this example approximately 19.85% of the metal is bound in a 1:2 metal to ligand ratio and the remainder is only bound in a 1:1 metal to ligand ratio. Further, a ratio of less than 1:1 would indicate the presence of unbound metal.

Step 4: Method Performance Study

Step 4.1—FT-IR Method Performance

Analytical Range & Percent Recovery

The analytical range and percent recovery of this method can be determined using varying mixtures of glycine (UL-TRAPURE available from Sigma Chemical Co.) and a sample picked at random, such as one produced at Albion Laboratories, Inc. manufacturing plant. By way of example, stock mixtures of a chelate and glycine are made and homogenized in the amalgamator, then a 1% sample in KBr are made from the stock mixtures. The samples are pressed into pellets and analyzed according to the procedures outlined above. Following this procedure, the absorbances were determined and are shown in Table 2.

TABLE 2

| Sample | % Glycine | % Copper Standard | % Glycine in pellet | Absorbance (911 cm$^{-1}$) |
|---|---|---|---|---|
| 1/99 | 96.88 | 1.04 | 0.969 | 1.07 |
| 5/95 | 93.99 | 5.02 | 0.940 | 1.04 |
| 10/90 | 91.81 | 10.17 | 0.918 | 1.03 |
| 20/80 | 82.42 | 20.58 | 0.824 | 0.92 |
| 30/70 | 71.40 | 30.56 | 0.714 | 0.82 |
| 40/60 | 58.75 | 39.23 | 0.588 | 0.67 |
| 50/50 | 52.43 | 52.51 | 0.524 | 0.54 |
| 60/40 | 40.79 | 61.13 | 0.408 | 0.44 |
| 70/30 | 29.95 | 69.96 | 0.299 | 0.32 |
| 80/20 | 19.58 | 78.36 | 0.196 | 0.22 |
| 85/15 | 14.70 | 83.25 | 0.147 | 0.16 |
| 90/10 | 10.37 | 93.65 | 0.104 | 0.12 |
| 95/5 | 5.08 | 96.89 | 0.051 | 0.06 |
| 99/1 | 0.97 | 99.84 | 0.010 | 0.05 |
| 100 Cu00112 | 0 | 100 | 0.000 | 0.04 |

These absorbances can be plotted against the percent glycine in the sample and the following correlation obtained: y=109.64x+0.0123, where y is the absorbance at 504 cm$^{-1}$, and x is the percent glycine by weight. The correlation coefficient of the line is 0.9980 indicating that the method is linear through the range analyzed. When the absorbances are inserted into the equation of the line from the standard curve, the following concentrations are obtained and shown in Table 3.

TABLE 3

| Sample | % Glycine in pellet | Calculated Glycine Concentration | % Recovery |
|---|---|---|---|
| 1/99 | 0.969 | 0.936% | 96.57% |
| 5/95 | 0.940 | 0.909% | 96.75% |
| 10/90 | 0.918 | 0.901% | 98.10% |
| 20/80 | 0.824 | 0.805% | 97.62% |
| 30/70 | 0.714 | 0.717% | 100.44% |
| 40/60 | 0.588 | 0.586% | 99.75% |
| 50/50 | 0.524 | 0.473% | 90.13% |
| 60/40 | 0.408 | 0.385% | 94.43% |
| 70/30 | 0.299 | 0.280% | 93.60% |
| 80/20 | 0.196 | 0.193% | 98.54% |
| 85/15 | 0.147 | 0.140% | 95.61% |
| 90/10 | 0.104 | 0.106% | 101.75% |
| 95/5 | 0.051 | 0.053% | 104.63% |
| 99/1 | 0.010 | 0.044% | 458.51% |
| 100 Cu001122 | 0.000 | 0.036% | |

Based on the data, the minimum limit of the method is at a 5% glycine-95% chelate (copper bisglycinate) mixture and the maximum limit of the method is 99% glycine-1% chelate. The percent recovery ranged anywhere from 90.13% to 104.63% in the analytical range from 99% glycine to 5% glycine. In the present example, samples containing less than 20% glycine will be shown. The analytical range that will be used is between 20%–1% unbound glycine. Therefore the free glycine can be quantified within 5% of the total glycine in the mixture, as the percent recovery in that range varies from 95.61%–104.63%.

Limits of Quantification and Detection

The limits of quantification and detection can be determined by scanning ten different blank pellets, containing only KBr. By way of example, the absorbances of the blanks, provided herein by example, are shown in Table 4.

TABLE 4

| Blanks | 504 abs |
|---|---|
| 1 | 0.0025 |
| 2 | 0.0023 |
| 3 | 0.0038 |
| 4 | 0.0026 |
| 5 | 0.0026 |
| 6 | 0.0022 |
| 7 | 0.0041 |
| 8 | 0.0035 |
| 9 | 0.0031 |
| 10 | 0.0027 |
| S.D. | 0.0007 |
| Ave | 0.0029 |

The limit of quantification is defined as $X+3\sigma$, where X is the average signal of the blanks and $\sigma$ is the standard deviation of the blanks. Therefore, the limit of quantification is $$\text{Limit of quantification} = X + 3\sigma$$
$$= 0.0029 + 3(0.0007)$$
$$= 0.0049$$

The limit of detection is defined as $X+10\sigma$, where X is the average signal of the blanks and $\sigma$ is the standard deviation of the blanks. Therefore, the limit of detection is $$\text{Limit of detection} = X + 10\sigma$$
$$= 0.0029 + 10(0.0007)$$
$$= 0.0095$$

Repeatability

The repeatability of this method can be determined by selecting four different samples at random and analyzing them four times. By way of the present examples, the four samples selected were Fe 00812, Fe 92443, Cu 91862, and Ca 92662. The absorbances, concentrations and statistical data are presented below in Table 5.

TABLE 5

Repeatability Study

| Maac | 504 Abs | Conc | % Free Glycine | Std. Dev. | Average | r.s.d. % |
|---|---|---|---|---|---|---|
| Cu00611 | 0.0280 | 0.018% | 1.79% | 0.0010 | 0.0193 | 5.151% |
|  | 0.0295 | 0.019% | 1.92% |  |  |  |
|  | 0.0308 | 0.020% | 2.02% |  |  |  |
|  | 0.0302 | 0.020% | 1.97% |  |  |  |
| Cu91862 | 0.0304 | 0.020% | 1.99% | 0.0007 | 0.0199 | 3.325% |
|  | 0.0300 | 0.020% | 1.96% |  |  |  |
|  | 0.0298 | 0.019% | 1.94% |  |  |  |
|  | 0.0316 | 0.021% | 2.09% |  |  |  |
| Fe00812 | 0.0496 | 0.036% | 3.57% | 0.0024 | 0.0361 | 6.648% |
|  | 0.0464 | 0.033% | 3.31% |  |  |  |
|  | 0.0533 | 0.039% | 3.87% |  |  |  |
|  | 0.0513 | 0.037% | 3.71% |  |  |  |
| Fe92443 | 0.0606 | 0.045% | 4.47% | 0.0036 | 0.0423 | 8.719% |
|  | 0.0557 | 0.041% | 4.07% |  |  |  |
|  | 0.0522 | 0.038% | 3.78% |  |  |  |
|  | 0.0619 | 0.046% | 4.58% |  |  |  |

The method consistently shows a standard deviation of less than 0.0036 and a relative standard deviation of less than 8.72%.

Step 4.2—ICP-MS Method Performance

The ICP-MS method can be carried out on a daily basis. In accordance with the present example, the data in Table 6 was calculated using daily duplicate samples.

TABLE 6

Limits of Quantification and Detection

| Element | Limit of Quantification (ppb) | Limit of Detection (ppb) |
|---|---|---|
| Boron | 22 | 7 |
| Calcium | 25 | 8 |
| Chromium | 0.6 | 0.2 |
| Cobalt | 0.2 | 0.07 |
| Copper | 6 | 2 |
| Iron | 18 | 6 |
| Magnesium | 26 | 9 |
| Manganese | 0.5 | 0.2 |
| Phosphorous | 12 | 4 |
| Potassium | 12 | 4 |
| Sodium | 12 | 4 |
| Zinc | 7 | 2 |

Repeatability

The number of samples in Table 7 refers to samples that contain analyte concentrations above the quantification limit.

TABLE 7

| Element | Number of samples | % CV Low | % CV High |
|---|---|---|---|
| Boron | 4 | 2.21% | 18.11% |
| Calcium | 18 | 0.24% | 7.87% |
| Chromium | 1 | 1.85% | 1.85% |
| Cobalt | 2 | 3.41% | 6.18% |
| Copper | 8 | 1.40% | 10.50% |
| Iron | 10 | 0.97% | 9.33% |
| Magnesium | 18 | 0.37% | 7.54% |
| Manganese | 15 | 0.08% | 13.11% |
| Phosphorous | 14 | 0.78% | 11.50% |
| Potassium | 12 | 1.99% | 19.54% |
| Sodium | 6 | 0.31% | 11.35% |
| Zinc | 11 | 0.21% | 15.61% |

Standard Curves

The standard curves all exhibited a correlation coefficient of >0.9951.

Analytical Range & Percent Recovery Samples

With respect to the exemplified data, the analytical range of the method was determined to be 99% to 5% unbound glycine in a sample formulated to a 1% concentration in KBr. The percent recovery ranged from 95.61% to 104.63% in the analytical range used.

Blanks

The absorbances of the blank pellets are all essentially zero, since the sample absorbances were calculated to 0.01 absorbance units and all blanks are less than 0.01 absorbance units.

Repeatability Samples

The method repeatability demonstrats a standard deviation of less than 0.0037 in all studies. The relative standard deviations, by way of example, are less than 8.72%.

CONCLUSIONS

The present method demonstrates the ability to quantify the amount of glycine bound, and through calculation, the amount of mineral bound in a solid chelate sample.

This method demonstrates acceptable reproducibility and recovery for quantification of chelation to at least 95% of glycine bound in a solid sample. As stated previously, the state of the sample during analysis is a factor in determining the true measurement of chelation. If the product is to be sold in a solid state, it should be measured in a solid state, because an aqueous measurement of the sample could be very misleading, as presented previously.

Further, it can be shown that glycine amino acid chelates demonstrate the 1643 cm$^{-1}$ peaks, which prove the metals are chelated by the glycine ligands in a bidentate manner, rather than just unidentate metals complexes. It should be noted that this peak demonstrated at 1643 wavenumbers is only seen in glycino-metal complexes and has not been observed with other metal amino acid complexes.

It should also be mentioned that any sample that is measured with this procedure, should first have the presence and amount of glycine proven. This method demonstrates the amount of glycine bound to the metal by measuring the amount of free glycine in the powdered sample. A sample that does not contain glycine, or contains very little glycine, could appear to be completely chelated according to this method, when in fact it may not be. Therefore, a quantitative glycine analysis should be conducted if this method were to be performed on samples other than on known chelates.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. A method of determining the amount of metal amino acid chelate present in a composition, comprising the steps of:
    (a) providing a composition having a predetermined amount of amino acid and a predetermined amount of a mineral;
    (b) determining the total amount of amino acid present in the composition that is bound to the mineral at a terminal COO$^-$ group of individual amino acid molecules using a spectrophotometer;
    (c) determining total mineral to total amino acid ratio;
    (d) determining the amount of the mineral that is unbound in the composition; and
    (e) determining the percent of chelation in the composition.

2. A method as in claim 1, wherein the amino acid is selected from the group consisting of glycine, alanine, arginine, asparagine, aspartic acid, cysteine, cystine, glutamine, glutamic acid, histidine, hydroxyproline, isoleucine, leucine, lysine, methionine, ornithine, phenylalanine, proline, seine, threonine, tryptophan, tyrosine, valine, and combinations thereof.

3. A method as in claim 2, wherein the amino acid is glycine.

4. A method as in claim 1, wherein the mineral is selected from the group consisting of copper, zinc, manganese, iron, magnesium, cobalt, chromium, molybdenum, and combinations thereof.

5. A method as in claim 4, wherein the mineral is copper.

6. A method as in claim 3, wherein the step of determining the total amount of amino acid present in the composition is carried out by FT-IR, and further comprises the step of comparing the difference between free amino acid present in the composition and chelate bound amino acid present in the composition.

7. A method as in claim 6, wherein the comparison of free glycine and chelate bound glycine is provided by a linear relationship in peak size at 504 cm−1 using FT-IR analysis.

8. A method in accordance with claim 6, wherein the step of determining the total mineral to total amino acid ratio comprises the steps of:
    a) determining the total metal content of the composition; and
    b) determining total ligand content based on nitrogen content, wherein the total metal content and the total nitrogen content are measured using a ICP-MS analysis.

9. A method in accordance with claim 7, wherein the step of determining the amount of the mineral that is unbound in the composition comprises the steps of:
    a) multiplying the percent of bound glycine by the total mineral to total amino acid ratio to obtain a total mineral to bound amino acid ratio; and
    b) determining the amount of unbound mineral using the bound amino acid ratio.

* * * * *